(12) United States Patent
Zwanziger et al.

(10) Patent No.: US 6,319,665 B1
(45) Date of Patent: Nov. 20, 2001

(54) HOME TEST KIT AND METHOD WITH TELEPHONE VERIFICATION OF RESULTS

(75) Inventors: Ron Zwanziger, Newton; Kenneth D. Legg, Wellesley, both of MA (US)

(73) Assignee: Inverness Medical Technology, Inc., Waltham, MA (US)

( * ) Notice: Subject to any disclaimer, the term of this patent is extended or adjusted under 35 U.S.C. 154(b) by 0 days.

(21) Appl. No.: 08/255,008

(22) Filed: Jun. 7, 1994

(51) Int. Cl.$^7$ ..................................................... C12Q 1/70
(52) U.S. Cl. .................. 435/5; 435/7.1; 435/7.8; 435/7.9; 435/7.92; 435/7.93; 435/7.94; 435/7.95; 435/974; 436/528; 436/530; 422/55; 422/56; 422/57; 422/58; 422/60; 422/61
(58) Field of Search ................... 435/5, 7.1, 7.8, 435/7.9, 7.92–7.95, 974, 528, 530; 422/55–58, 60, 61

(56) References Cited

U.S. PATENT DOCUMENTS

| | | | |
|---|---|---|---|
| 4,178,360 | 12/1979 | Cleeland et al. | 424/1 |
| 4,535,057 | 8/1985 | Dreesman et al. | 435/5 |
| 4,818,678 | 4/1989 | Oldstone et al. | 435/5 |
| 4,818,688 | 4/1989 | Adamich et al. | 435/7 |
| 4,837,167 | 6/1989 | Schoemaker et al. | 436/513 |
| 4,838,275 | 6/1989 | Lee | 128/670 |
| 4,839,288 | 6/1989 | Montagnier et al. | 435/235 |
| 4,855,224 | 8/1989 | Berman et al. | 435/5 |
| 4,879,219 | 11/1989 | Wands et al. | 435/7 |
| 4,888,290 | 12/1989 | Kortright et al. | 435/240.27 |
| 4,917,998 | 4/1990 | Burger et al. | 435/5 |
| 4,918,166 | 4/1990 | Kingsman et al. | 530/350 |
| 4,921,787 | 5/1990 | Riggin et al. | 435/5 |
| 4,983,529 | 1/1991 | Stewart et al. | 436/512 |
| 5,001,049 | 3/1991 | Klein et al. | 435/5 |
| 5,008,183 | 4/1991 | Osther | 435/5 |
| 5,104,790 | 4/1992 | Flesher et al. | 435/5 |
| 5,135,864 | 8/1992 | Montagnier et al. | 435/235.1 |
| 5,141,850 | 8/1992 | Cole et al. | 436/525 |
| 5,156,949 | 10/1992 | Luciw et al. | 435/5 |
| 5,173,399 | 12/1992 | Mehta et al. | 435/5 |
| 5,188,937 | 2/1993 | Schulte et al. | 435/7 |
| 5,204,095 | 4/1993 | Goodall et al. | 424/86 |
| 5,208,321 | 5/1993 | Hovanessian et al. | 530/350 |
| 5,221,610 | 6/1993 | Montagnier et al. | 435/7.1 |
| 5,252,459 | 10/1993 | Tarcha et al. | 435/6 |
| 5,256,561 | 10/1993 | Chin | 435/240.27 |
| 5,260,189 | 11/1993 | Formoso et al. | 435/5 |
| 5,281,395 | 1/1994 | Markart et al. | 422/82.05 |
| 5,413,764 | 5/1995 | Haar | 422/82.09 |

FOREIGN PATENT DOCUMENTS

| | | |
|---|---|---|
| 0392283 | 10/1990 | (EP) . |
| 0492326 | 7/1992 | (EP) . |
| 88/10272 | 12/1988 | (WO) . |
| 92/21977 | 12/1992 | (WO) . |

OTHER PUBLICATIONS

Promotional Materials for CAPILLUS HIV Test, Cambridge Biotech Corp. (undated).

*Primary Examiner*—Jeffrey Stucker
(74) *Attorney, Agent, or Firm*—Oppedahl & Larson LLP

(57) ABSTRACT

Self-testing for a disease or physiological condition is achieved by having the individual being tested obtain a sample of physiological fluid, e.g., blood, urine, sputum or saliva, from him or herself. The sample is introduced into an assay system which produces a coded pattern indicative of the presence or a different coded pattern indicative of the absence of the disease or physiological condition. The individual then transmits the coded pattern to a remote location, for example by making a telephone call to an interpretation center, and receives from the remote location an interpretation of the coded pattern together with any counseling which may be appropriate in view of the interpretation of the coded pattern. The coded patterns are selected such that the individual may not interpret the test results without consulting the interpretation center. Further, the assay system employed is advantageously made so that the coded patterns indicative of a positive or negative result are dependent on an identifier, such as a lot number or serial number, assigned to the assay system or kit containing the assay system.

26 Claims, 3 Drawing Sheets

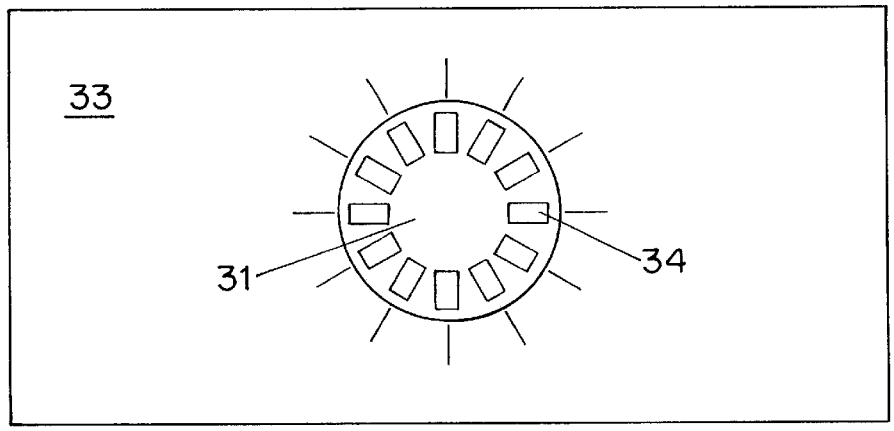
FIG. 5A
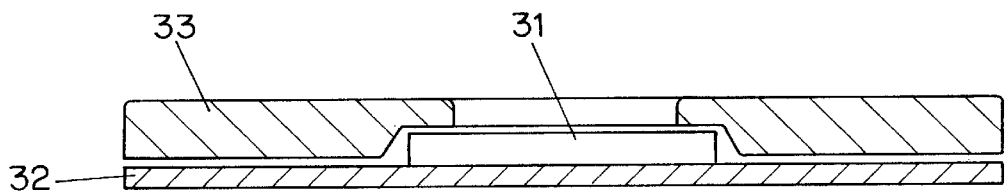
FIG. 5B
```
X X X X      X X X X      X - - -
O - - X      O - - X      X - - -
O X X X      O - - X      X - - -
O - - X      O - - X      X - - -
X X X X      O O O X      X - - -
```
FIG. 6

HOME TEST KIT AND METHOD WITH TELEPHONE VERIFICATION OF RESULTS

This application relates to a test kit for use in the detection of diseases, hormone levels, and other physiological conditions, and in particular to a test kit for home use in circumstances such as detection of HIV infections where counseling is considered necessary or desirable in the event of a positive result.

Increasingly, assays for the detection of disease-causing organisms and physiological conditions are becoming simplified such that testing can be performed by the individual patient without the involvement of a medical professional. Such testing by the individual is desirable because it can reduce the costs, and provide an immediate answer to an individual's health concerns without the need to schedule an appointment with a medical professional or to await the processing of a sample by a laboratory. Moreover, many individuals prefer the privacy afforded by performing tests in their own home. Nevertheless, in some circumstances, the significance of the test result may be such that it is deemed necessary or desirable to provide counseling to the individual at the time the test result is obtained. This requirement for counseling has meant that the privacy and reduced costs associated with home testing have not been available for some types of tests.

It is an object of the present invention to provide a home test kit which facilitates the delivery of any necessary counseling as a result of the outcome of the test.

It is a further object of the invention to provide a home test kit for HIV infections which facilitates the delivery of any necessary counseling as a result of the outcome of the test.

To provide methods of making kits for use in accordance with the invention, and a method of performing home testing where any necessary counseling is provided to the individual at the same time that the results are conveyed.

SUMMARY OF THE INVENTION

These and other objects of the invention are achieved using a method for self-testing in which the individual being tested first obtains a sample of physiological fluid, e.g., blood, urine, sputum or saliva, from him or herself, and introduces the sample into an assay system which produces a coded pattern indicative of the presence or absence of the disease or physiological condition. The individual then transmits the coded pattern to a remote location, for example by making a telephone call to an interpretation center, and receives from the remote location an interpretation of the coded pattern together with any counseling which may be appropriate in view of the interpretation of the coded pattern.

The assay system employed in the method of the invention is advantageously made so that the coded patterns indicative of a positive or negative result are dependent on an identifier, such as a lot number or serial number, assigned to the assay system or kit containing the assay system. Linking the coded patterns, and thus the interpretation of the test result to the particular kit being used makes it necessary to utilize the remote location for interpretation in each instance, even if tests for the same disease or physiological condition have been performed by the same individual before.

BRIEF DESCRIPTION OF THE DRAWINGS

FIGS. 5A and 5B shows a further embodiment of the assay system in accordance with the invention; and FIG. 6 shows a type of numerical coded patterns useful in the invention.

DETAILED DESCRIPTION OF THE INVENTION

In order to provide a home test kit which can be performed at any time by the test subject rather than a medical professional, but which still affords the opportunity to provide counseling concerning the results of the test when necessary, the present invention makes use of assay systems in which the result is a coded pattern. The coded pattern cannot be interpreted directly by the user, but can be readily transmitted by the test user to a remote location for immediate interpretation.

Figure 1:
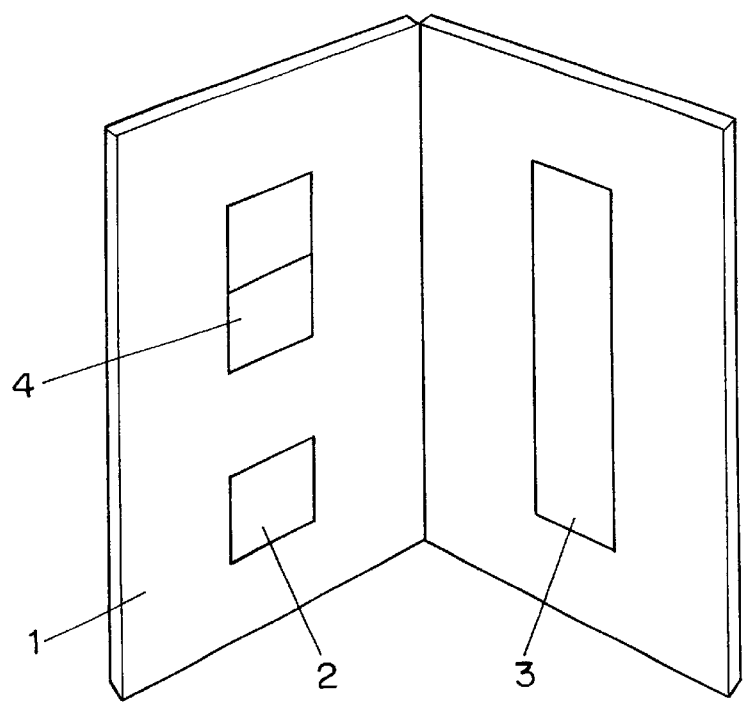
FIG. 1 shows an embodiment of an assay system in accordance with the invention.

Provided that a coded pattern results from the assay, the physical form of the assay system of the invention may be analogous to any of the various forms known in the art today. For example, FIG. 1 shows a first embodiment of an assay system in accordance with the invention. This system, known as the ICT format, is described in International Patent Publication WO 92/21977 which is incorporated herein by reference. Briefly, the assay system shown in FIG. 1 is formed on a foldable support 1. One side of the foldable support 1 has a sample preparation area 2, where the sample of physiological fluid is deposited. The other side of the physiological support has a chromatographic element 3. After placing the sample and a detection reagent on the sample preparation area, the support is folded to bring the preparation area into contact with the chromatographic support. The sample and the detection reagent are then permitted to migrate through the chromatographic element for a period of time sufficient to result in a visual indication of the test result through a window 4 formed in the foldable support. The window 4 has a plurality of reference marks, such as number or letters, written along the edges thereof to allow easy transmission of the coded pattern.

To use the device shown in FIG. 1, a sample and a test reagent are placed in the sample area. The sample is an appropriate physiological fluid. The test reagent includes an excess of a detectable material which binds specifically with a diagnostic constituent in the sample indicative of the disease or physiological condition. The detectable material may, for example, be an antibody or antigen which forms a specific binding pair with the constituent being tested for, and is desirably labeled with a visibly detectable material. Preferred visibly detectable materials are colloidal metals, particularly gold. Other visibly colored materials which may be used are dispersed dyes and colored latexes. The detectable material binds to any diagnostic constituent present in the sample, causing it to be labeled with the detectable material.

The chromatographic element 3 is formed in a manner which will result in a first coded pattern in the form of a plurality of bars when the test result is positive, and a second coded pattern, different from the first coded pattern, when the test result is negative. Suitable materials for the chromatographic element 3 are those which will result in the sample being drawn from the sample application location through the detection zone where the coded patterns are located. Examples of such materials include those material suitable as medium for thin-layer chromatography of analytes and analyte-antibody conjugates such as nitrocellulose, nylon, rayon, cellulose, paper and silica.

Figure 2:
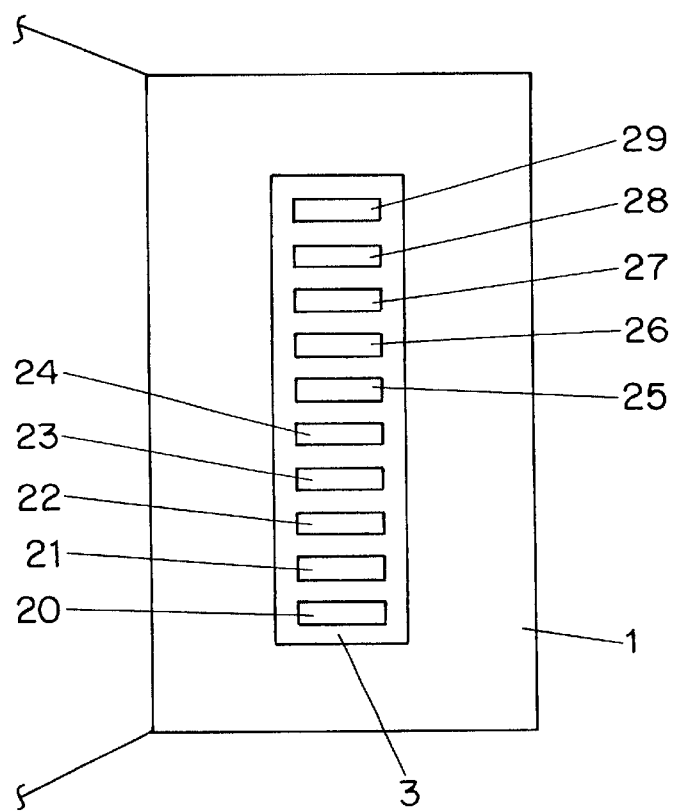
FIG. 2 shows a chromatographic element useful in the assay system of FIG. 1.
Figure 3:
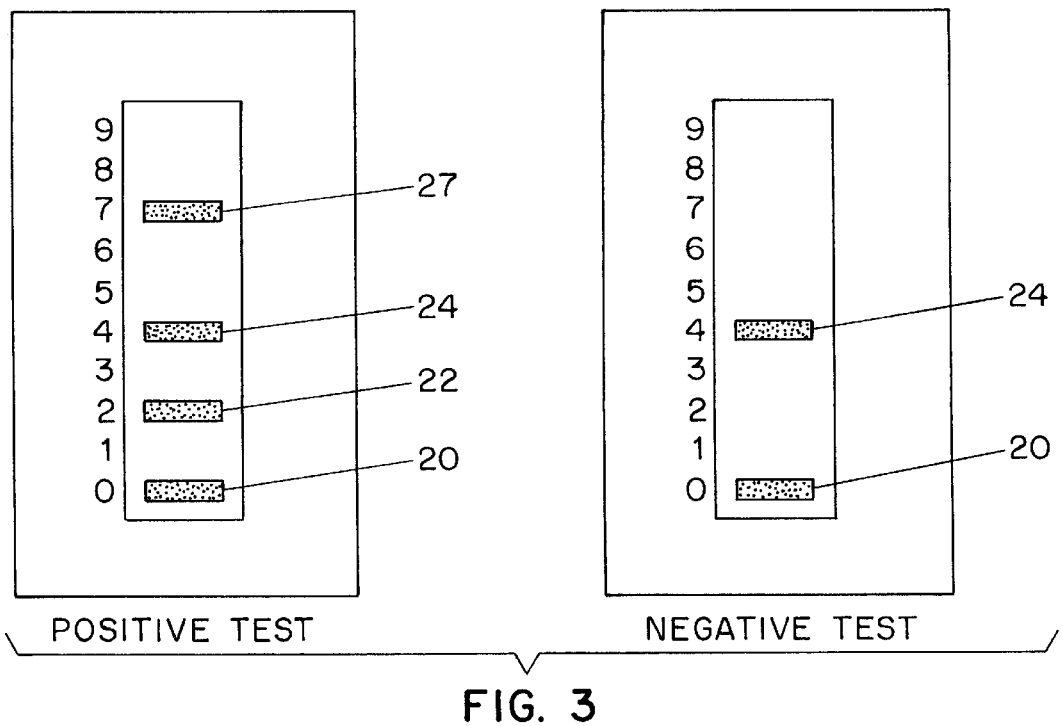
FIG. 3 shows exemplary positive and negative results for an assay system in accordance with the invention.

An example of the formation of coded patterns on a chromatographic element 3 including individual immunosorbent regions 20–29 is shown in FIG. 2. Some of the regions are selected as "control regions" which specifically bind to excess detectable material included in the reagent, or to one or more detectable control materials included in the test reagent. Others of the regions are constructed as "test indicator regions" which specifically bind to indicators of the disease or physiological condition. Some of the regions are specifically left empty, so that no line will form in these regions, regardless of the nature of the sample. For example, regions 20 and 24 might be selected as control regions and regions 22 and 27 selected as test indicator regions. The results of a positive and negative test using these regions, viewed through the window 4, are shown in FIG. 3. As shown, the negative test would result in a code number 04, while a positive test would result in a code number 0247. The result would be interpreted by transmitting the code number obtained from the test to an interpretation center at a remote location, and receiving advice from the interpretation center of the result of the test. For example, the interpretation center might be contacted by telephone, which would afford the opportunity for telephone counseling.

To further avoid the possibility of the user guessing, it is desirable to have the coded patterns corresponding to positive and negative results vary from kit to kit or from lot to lot of the product. Thus, a further aspect of the invention involves a method of preparing an assay system in which an identifier is first assigned to the system being prepared. An algorithm is then applied to this identifier to determine patterns which will correspond to positive and negative results. For example, a simple algorithm might assign the patterns based upon the last digit or digits of the identifier. In this case, the user would transmit not only the coded pattern resulting from the test but also the identifier of the particular kit used to the interpretation center. The interpretation center would then determine what the positive and negative codes should be for the particular kit used by the person transmitting the information and compare it to the actual result obtained to interpret the test results.

Figure 4:
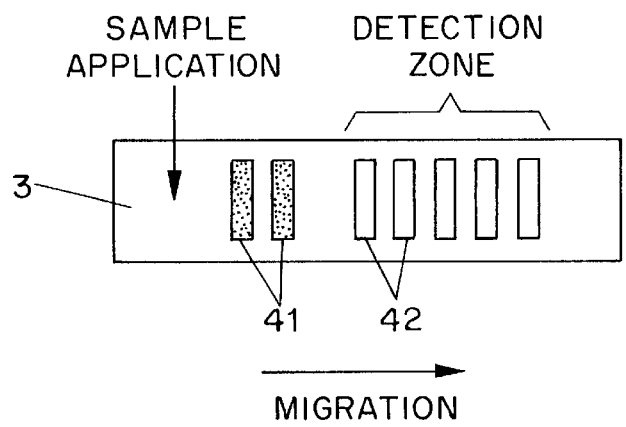
FIG. 4 shows an alternative format for an assay system in accordance with the invention.

While the ICT test format as described above is a preferred format for use in the present invention, the invention is not limited to this format alone. For example, other formats useful in the invention include the assay systems such as those disclosed in U.S. Pat. No. 5,141,850, incorporated herein by reference. In this format, as depicted in FIG. 4, the test reagents 41 and the immunosorbent regions 42 are formed as separate regions on a chromatographic element 3. Addition of a liquid sample solubilizes the test reagents and the sample and the test reagents together migrate through the porous carrier to a detection zone where the immunosorbent areas are located.

It will also be understood that while a preferred format of the invention involves the application of the sample and test reagents at one end of a chromatographic element, with the sample and test reagents being drawn along an elongated strip to a detection zone as shown in FIGS. 1 and 2, the invention also encompasses assay systems in which the sample and test reagents are applied directly to a detection zone and drawn through the chromatographic element to the extent not bound to the coded patterns applied to the chromatographic element. Thus, as shown in FIGS. 5A and 5B, an assay system in accordance with the invention may be formed as a circular chromatographic element 31 enclosed between a bottom support 32 and a cover 33. Immunosorbent regions 34 are formed on the surface of the disk in alignment with reference marks printed on the cover 33. When a sample and test reagents are applied into the opening in the cover, the liquid is drawn into the chromatographic element. Detectable test reagent is trapped on the surface of the chromatographic element, however, to the extent that it becomes bound to an immunosorbent region as a result of the presence of the selected diagnostic analyte.

Thus, in a generic sense, the assay system of the invention comprises a chromatographic element through which at least portions of the sample, including portions of the sample which are indicative of the disease or other physiological condition being tested for, and other test reagents migrate. The chromatographic element has at least two coded patterns formed on it, one indicative of a negative test and another indicative of a positive test, which cannot be distinguished in the absence of knowledge of the code.

Furthermore, while the invention is exemplified above using parallel lines and a set of associated reference marks, it will be understood that the patterns formed may be of any shape which permits the user to read a code to interpretation center personnel. For example, the patterns might be in the form a plurality of concentric rings, or might be deposited on the chromatographic element in patterns representing numbers or letters or other characters which would become visible when the assay system was used.

Thus, as shown in FIG. 6, a plurality of dots made up of control (X) and sample (O) regions can be used to form recognizable characters. The dashes indicates locations where no material is deposited. In FIG. 6, a positive test would yield the number 801, while a negative test would yield the number 371. The use of a control only number at the end away from the sample application ensures that migration of the sample has occurred through the entire chromographic element. Moreover, number or letter patterns can be selected to utilize a minimum number of dots in the sample areas, so that small amounts of material in the sample can be evaluated.

Alternatively, use of the assay system may result in characters which were initially visible being obscured.

The foregoing discussion of the methods, kits and devices of the invention is general in terms of the reagents employed, because the invention may be used to perform testing for any disease or physiological condition for which a sandwich type assay, i.e., an assay in which two specific binding partners are used to immobilize and label an analyte at a defined location, can be developed. To further exemplify the invention, however, the following non-limiting examples of specific applications are provided.

Detection of human immunodeficiency virus (HIV) is an example of a disease for which the present invention is advantageously employed because of the need for counseling for those who receive a positive test result. There are basically two ways in which such testing can be carried out using the present invention: detection of virus itself, and the detection of antibodies to the virus. In the case of detection of the virus itself, the immunosorbent regions on the chromatographic support are selected to specifically bind to the virus. For example, the test indicator regions and the labeled detection reagent may be an antibody which specifically binds to some portion of the HIV virus coat, such as those disclosed in U.S. Pat. Nos. 4,879,211; 4,888,290; 4,888,742; 4,917,998; 5,104,790; 5,173,399; 5,208,321; 5,256,561 which are incorporated herein by reference. The test indicator immunosorbent regions and the labeled detection reagent may also be formed from immunological active fragments of antibodies which specifically bind to the virus, such as those disclosed in U.S. Pat. No. 4,963,529 which is incorporated herein by reference.

In the case of detection of antibodies to the virus, the test indicator immunosorbent regions are preferably formed from peptides, proteins or glycoproteins which are immunologically cross-reactive with the intact virus, rather than with the intact virus, to avoid the possibility of including an infective agent in the test kit. Peptides which can serve this purpose are disclosed in U.S. Pat. Nos. 4,839,288; 4,921,787; 5,001,049; 5,156,949; 5,135,864; 5,260,189; 5,221,610; and 5,208,321 which are incorporated herein by reference. The detection test reagent is then suitably a labeled anti-human immunoglobulin.

Antibodies employed in the present invention as reagents may be polyclonal or monoclonal antibodies. Mixtures or "cocktails" of monoclonal antibodies or monoclonal and polyclonal antibody preparations may also be utilized. In this way, optimized mixtures of antibodies may be selected, so that several antibodies may be used binding to different epitopes of the same disease-associated material.

Because there are several significant variants of HIV, notably the variants referred to as HIV-1 and HIV-2, it may be desirable to form more than two coded patterns which include immunosorbent regions which are capable of distinguishing between the type of the virus detected and not merely identifying that an HIV virus of some type is present. Particular agents useful to detect HIV-1 include the peptides disclosed in U.S. Pat. No. 5,260,189 which reproduce immunoreactive regions of the gp41 and p24; and the monoclonal antibodies to HIV-1 p24 disclosed in U.S. Pat. No. 5,173,399. Particular agents useful to detect HIV-2 include the antibodies disclosed in U.S. Pat. No. 5,256,561, which bind to the gp36 antigen of HIV-2; the gp80 glycoprotein or antibodies thereto disclosed in U.S. Pat. No. 5,208,321; and the peptides disclosed in U.S. Pat. No. 5,260,189 which reproduce immunoreactive regions of the gp32 peptide.

In the case where multiple analytes in the sample are being evaluated, it may be desirable to have a single lebeled detection reagent which will bind to either of the analytes. When the analyte is an antibody from the sample, this is easily accomplished by use of a single labeled anti-human immunoglobulin. When the analytes are antigens, it may not be possible, unless, as in the case of HIV-1 and HIV-2 there are common epitopes between the two analytes.

It may also be desirable in the case of an HIV test to test for one or more disease commonly found in HIV infected individuals, particularly where such a disease may be associated with increased severity or early onset of symptomatic AIDS. Thus, additional coded patterns may be included on the chromatographic element to simultaneously test for hepatitis, herpes, chlamydia, toxoplasmosis, rubella, cytomegalovirus or other disease of interest. Antibodies or antigens for such diseases useful in diagnosis of such disease are known, for example from U.S. Pat. Nos. 5,204,095; 5,188,937; 5,030,562; 5,008,183; 4,879,219; 4,855,224; 4,837,167; 4,818,688; 4,818,678; 4,535,057; and 4,178,360, which are incorporated herein by reference.

While testing for HIV infections is a significant utility for the present invention, the invention is not limited to this use. Other conditions which might be evaluated using the method of the invention include the disease mentioned above individually or any other conditions where counseling is considered desirable. Indeed, it will be apparent to the person skilled in the art that the present invention is applicable to all tests for antibodies or antigens detectable through specific binding assays.

We claim:
1. A kit comprising
   (a) an assay system for use in testing for a disease or a physiological condition, comprising a chromatographic element having a plurality of specific binding regions defined thereon to define a first coded pattern indicative of a positive test and a second coded pattern, different from the first coded pattern, and indicative of a negative test, wherein the result of the test cannot be interpreted in absence of knowledge of the code; and
   (b) an instruction sheet with directions for use of the assay printed thereon, said instruction sheet not including knowledge of the code sufficient to permit interpretation of the test result.

2. A kit according to claim 1, wherein first and second coded patterns are each formed from a plurality of parallel lines.

3. A kit according to claim 1, wherein the first coded pattern is formed from an antibody which specifically binds to a component of a physiological fluid which is diagnostic for the disease or physiological condition being tested for.

4. A kit according to claim 1, wherein the first coded pattern is formed from an antigen or hapten which specifically binds to an antibody which is diagnostic for the disease or physiological condition being tested for.

5. A kit according to claim 1, wherein the specific binding regions making up the first coded pattern specifically bind to at least one epitope of human immunodeficiency virus.

6. A kit according to claim 5, wherein the specific binding regions making up the first coded pattern are formed from a monoclonal antibody.

7. A kit according to claim 1, wherein the specific binding regions making up the first coded pattern specifically bind to an antibody to at least one epitope of human immunodeficiency virus.

8. A kit according to claim 1, wherein the chromatographic element has a third coded pattern formed thereon indicative of a second disease or physiological condition.

9. A kit according to claim 8, wherein the specific binding regions making up the first coded pattern specifically bind to at least one epitope of human immunodeficiency virus.

10. A kit according to claim 9, wherein the specific binding regions making up the first coded pattern specifically bind to an epitope specific for HIV-1 and the specific binding regions making up the third coded pattern specifically bind to an epitope specific for HIV-2.

11. A kit according to claim 10, wherein the specific binding regions making up the first and third coded patterns are formed from monoclonal antibodies.

12. A kit according to claim 9, wherein the specific binding regions making up the first and third coded pattern are formed from monoclonal antibodies.

13. A kit according to claim 8, wherein the specific binding regions making up the first coded pattern specifically bind to an antibody to at least one epitope of human immunodeficiency virus.

14. A kit according to claim 13, wherein the specific binding regions making up the first coded pattern specifically bind to an antibody to an epitope specific for HIV-1 and the specific binding regions making up the third coded pattern specifically bind to an antibody to an epitope specific for HIV-2.

15. A method for self-testing by an individual for a disease or physiological condition, wherein the individual being tested performs the following steps:

(a) obtaining a sample of physiological fluid from him or herself;

(b) introducing the sample into an assay system effective to produce a first coded pattern indicative of the presence of the disease or a second coded pattern, different from the first coded pattern in the absence of the disease or physiological condition;

(c) transmitting the coded pattern resulting from introduction of the sample into the assay system to a remote location for interpretation; and (d) receiving from the remote location an interpretation of the coded pattern together with any counseling which may be appropriate in view of the interpretation of the coded pattern.

16. A method according to claim 15, wherein the coded pattern is transmitted and the interpretation of the coded pattern is received by telephone.

17. A method for preparing a home test kit for a disease or physiological conditions comprising the steps of:

(a) assigning an identification number to the kit;

(b) determining a first coded pattern indicative of a positive result in the test and a second coded pattern indicative of a negative result, said first and second coded patterns being determined based upon the identification number assigned to the kit; and (c) applying test reagents to a carrier in such a manner that the first coded pattern will be obtained if a positive sample is analyzed with the kit and the second coded pattern will be obtained if a negative sample is analyzed by the kit.

18. A method according to claim 17, wherein the identification number is a serial number unique to the kit being prepared.

19. A method according to claim 17, wherein the first and second coded patterns are each formed from a plurality of substantially parallel lines of reagent applied to the carrier.

20. A method according to claim 19, wherein the lines are applied to the carrier in alignment with a plurality of reference marks.

21. A method according to claim 20, wherein the reference marks are numbers.

22. A method according to claim 17, wherein the reagents are selected to yield a positive result in the presence of human immunodeficiency virus.

23. A method according to claim 17, wherein the reagents are selected to yield a positive result in the presence of antibodies to human immunodeficiency virus.

24. A kit according to claim 1, wherein the first and second coded patterns are easily described verbally by a user.

25. A method according to claim 17, further comprising the step of packaging the carrier having the first and second coded patterns applied thereto with an instruction sheet with directions for use of the kit printed thereon, said instruction sheet not including knowledge of the code sufficient to permit interpretation of the test result.

26. A method according to claim 15, wherein the first and second coded patterns cannot be interpreted by the individual in the absence of transmitting the coded pattern to the remote location.

* * * * *